United States Patent [19]

Kleemann et al.

[11] Patent Number: 5,807,804
[45] Date of Patent: Sep. 15, 1998

[54] SUBSTITUTED PYRIDINE HERBICIDAL AGENTS

[75] Inventors: Axel Kleemann, Hanau; Helmut Siegfried Baltruschat, Schweppenhausen, both of Germany

[73] Assignee: American Cyanamid Company, Madison, N.J.

[21] Appl. No.: 801,598

[22] Filed: Feb. 13, 1997

Related U.S. Application Data

[60] Provisional application No. 60/012,055, Feb. 22, 1995.

[51] Int. Cl.$^6$ ............... A01N 43/40; C07D 403/12; C07D 401/12
[52] U.S. Cl. ............... 504/244; 514/341; 546/275.1
[58] Field of Search ............... 546/275.1; 504/244; 514/341

[56] References Cited

U.S. PATENT DOCUMENTS 3,535,328  10/1970  Zielinski ............... 346/268.1

FOREIGN PATENT DOCUMENTS

| | | | |
|---|---|---|---|
| 447004 | 3/1991 | European Pat. Off. | C07D 213/81 |
| 488474 | 11/1991 | European Pat. Off. | C07D 213/86 |
| 537816 | 9/1992 | European Pat. Off. | C07D 213/81 |
| 572093 | 5/1993 | European Pat. Off. | C07D 213/69 |
| 692 474 A1 | 1/1996 | European Pat. Off. | C07D 213/84 |
| WO 94/22833 | 10/1994 | WIPO | C07D 213/69 |

*Primary Examiner*—Alan L. Rotman
*Attorney, Agent, or Firm*—Joseph M. Mazzarese

[57] ABSTRACT

There are provided substituted pyridine compounds having the structural formula I

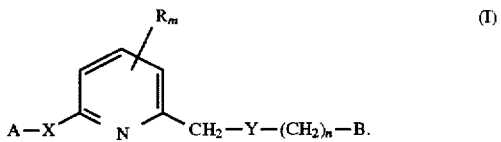

Further provided are compositions and methods comprising those compounds for the control of undesirable plant species.

17 Claims, No Drawings

SUBSTITUTED PYRIDINE HERBICIDAL AGENTS

This application claims priority from the co-pending provisional application 60/012,055 filed Feb. 22, 1996.

BACKGROUND OF THE INVENTION

Weeds cause tremendous global economic losses by reducing crop yields and lowering crop quality. In the United States alone, agronomic crops must compete with hundreds of weed species.

In spite of the commercial herbicides available today, damage to crops caused by weeds still occurs. Accordingly, there is ongoing research to create new and more effective herbicides.

Certain pyridine derivatives are known to have herbicidal activity (U.S. Pat. No. 3,535,328; EP-A2-447004; EP-A1-488474; EP-A1-537816; and EP-A1-572093). However, none of those publications describe the herbicidal agents of the present invention.

It is therefore an object of the present invention to provide compounds which are effective for controlling undesirable plant species.

It is also an object of the present invention to provide methods for controlling undesirable plant species.

Those and other objects of the present invention will become more apparent from the detailed description thereof set forth below.

SUMMARY OF THE INVENTION

The present invention describes substituted pyridine compounds which are useful as herbicidal agents.

The substituted pyridine compounds of the present invention have the structural formula I

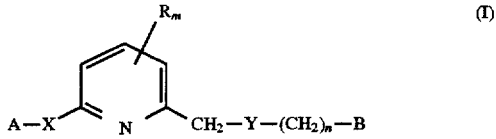

wherein
A and B are each independently
  phenyl optionally substituted with one or more halogen atoms, nitro groups, cyano groups, amino groups, hydroxyl groups, $C_1$–$C_4$alkyl groups, $C_1$–$C_4$haloalkyl groups, $C_1$–$C_4$alkoxy groups, $C_1$–$C_4$haloalkoxy groups or $C_1$–$C_4$haloalkylsulfonyl groups,
  1- or 2-naphthyl optionally substituted with one or more halogen atoms, nitro groups, cyano groups, amino groups, hydroxyl groups, $C_1$–$C_4$alkyl groups, $C_1$–$C_4$haloalkyl groups, $C_1$–$C_4$alkoxy groups, $C_1$–$C_4$haloalkoxy groups or $C_1$–$C_4$haloalkylsulfonyl groups, or
  a 5- or 6-membered nitrogen-containing heteroaromatic ring optionally substituted with one or more halogen atoms, nitro groups, cyano groups, amino groups, hydroxyl groups, $C_1$–$C_4$alkyl groups, $C_1$–$C_4$haloalkyl groups, $C_1$–$C_4$alkoxy groups, $C_1$–$C_4$haloalkoxy groups or $C_1$–$C_4$haloalkylsulfonyl groups;
X and Y are each independently O or S;
R is $C_1$–$C_6$alkyl, $C_1$–$C_6$haloalkyl, $C_1$–$C_6$alkoxy, $C_1$–$C_6$haloalkoxy, $C_1$–$C_6$alkylthio or di($C_1$–$C_6$alkyl)amino;
m is an integer of 0, 1 or 2; and
n is an integer of 0 or 1.

This invention also relates to compositions containing those compounds and methods for using those compounds and compositions. Advantageously, it has been found that the compounds of the present invention, and compositions containing them, are useful for the control of undesirable plant species.

DETAILED DESCRIPTION OF THE INVENTION

The present invention provides a method for controlling undesirable plant species which comprises applying to the foliage of said plants or to the soil or water containing seeds or other propagating organs thereof, a herbicidally effective amount of a formula I, substituted pyridine compound.

The substituted pyridine compounds of the present invention have the structural formula I

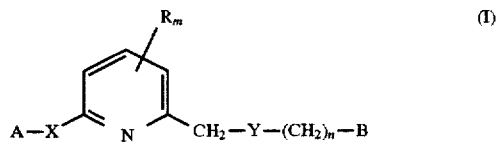

wherein
A and B are each independently
  phenyl optionally substituted with one or more halogen atoms, nitro groups, cyano groups, amino groups, hydroxyl groups, $C_1$–$C_4$alkyl groups, $C_1$–$C_4$haloalkyl groups, $C_1$–$C_4$alkoxy groups, $C_1$–$C_4$haloalkoxy groups or $C_1$–$C_4$haloalkylsulfonyl groups,
  1- or 2-naphthyl optionally substituted with one or more halogen atoms, nitro groups, cyano groups, amino groups, hydroxyl groups, $C_1$–$C_4$alkyl groups, $C_1$–$C_4$haloalkyl groups, $C_1$–$C_4$alkoxy groups, $C_1$–$C_4$haloalkoxy groups or $C_1$–$C_4$haloalkylsulfonyl groups, or
  a 5- or 6-membered nitrogen-containing heteroaromatic ring optionally substituted with one or more halogen atoms, nitro groups, cyano groups, amino groups, hydroxyl groups, $C_1$–$C_4$alkyl groups, $C_1$–$C_4$haloalkyl groups, $C_1$–$C_4$alkoxy groups, $C_1$–$C_4$haloalkoxy groups or $C_1$–$C_4$haloalkylsulfonyl groups;
X and Y are each independently O or S;
R is $C_1$–$C_6$alkyl, $C_1$–$C_6$haloalkyl, $C_1$–$C_6$alkoxy, $C_1$–$C_6$haloalkoxy, $C_1$–$C_6$alkylthio or di($C_1$–$C_6$alkyl)amino;
m is an integer of 0, 1 or 2; and
n is an integer of 0 or 1.

Preferred formula I substituted pyridine compounds of this invention are those wherein
A and B are each independently
  phenyl optionally substituted with one or more halogen atoms, $C_1$–$C_4$alkyl groups, $C_1$–$C_4$haloalkyl groups, $C_1$–$C_4$alkoxy groups, $C_1$–$C_4$haloalkoxy groups or $C_1$–$C_4$haloalkylsulfonyl groups, or a pyridyl, pyrazolyl, imidazolyl, triazolyl, isoxazolyl, tetrazolyl, pyrazinyl, pyridazinyl or triazinyl group each optionally substituted with one or more halogen atoms, $C_1$–$C_4$alkyl groups, $C_1$–$C_4$haloalkyl groups, $C_1$–$C_4$alkoxy groups, $C_1$–$C_4$haloalkoxy groups or $C_1$–$C_4$haloalkylsulfonyl groups;
X and Y are each independently O or S;
R is $C_1$–$C_4$alkyl, $C_1$–$C_4$haloalkyl, $C_1$–$C_4$alkoxy, $C_1$–$C_4$haloalkoxy, $C_1$–$C_4$alkylthio or di($C_1$–$C_4$alkyl)amino; and
m and n are each independently an integer of 0 or 1.

More preferred formula I herbicidal agents of the present invention are those wherein A and B are each independently phenyl optionally substituted with one to three halogen atoms, $C_1-C_4$alkyl groups or $C_1-C_4$haloalkyl groups, or a pyridyl or pyrazolyl group each optionally substituted with one to three halogen atoms, $C_1-C_4$alkyl groups or $C_1-C_4$haloalkyl groups;

X and Y are O;

R is $C_1-C_4$alkyl, $C_1-C_4$haloalkyl, $C_1-C_4$alkoxy or $C_1-C_4$haloalkoxy; and m and n are each independently an integer of 0 or 1.

Most preferred formula I herbicidal agents of the present invention are those wherein A is phenyl optionally substituted with one chlorine atom or trifluoromethyl group, 4-pyridyl optionally substituted with one chlorine atom or trifluoromethyl group, or 5-pyrazolyl optionally substituted with one or two methyl groups or trifluoromethyl groups;

B is phenyl optionally substituted with one or two fluorine atoms, chlorine atoms, methyl groups or trifluoromethyl groups, 2- or 4-pyridyl optionally substituted with one or two fluorine atoms, chlorine atoms, methyl groups or trifluoromethyl groups, or 5-pyrazolyl optionally substituted with one or two methyl groups or trifluoromethyl groups;

X and Y are O; and m and n are 0.

Substituted pyridine compounds of the present invention which are particularly effective herbicidal agents include 2-[(2-chloro-4-pyridyl)oxy]-6-{[(2-chloro-4-pyridyl)oxy]-methyl}pyridine;

2-[(2-chloro-4-pyridyl)oxy]-6-{[(α,α,α-trifluoro-m-tolyl)oxy]methyl}pyridine;

2-[(α,α,α,-trifluoro-m-tolyl)oxy]-6-{[(α,α,α-trifluoro-m-tolyl)oxy]methyl}pyridine;

2-{[(2-chloro-4-pyridyl)oxy]methyl}-6-[(α,α,α-trifluoro-m-tolyl)oxy]pyridine;

2-{[(6-chloro-2-pyridyl)oxy]methyl}-6-[(α,α,α-trifluoro-m-tolyl)oxy]pyridine;

2-[(m-fluorophenoxy)methyl]-6-[(α,α,α-trifluoro-m-tolyl)oxy]pyridine;

2-[(m-fluorophenoxy)methyl]-6-{[1-methyl-3-(trifluoromethyl)pyrazol-5-yl]oxy}pyridine;

2-[(p-fluorophenoxy)methyl]-6-{[1-methyl-3-(trifluoromethyl)pyrazol-5-yl]oxy}pyridine;

2-{[1-methyl-3-(trifluoromethyl)pyrazol-5-yl]oxy}-6-[(o-tolyloxy)methyl]pyridine;

2-{[1-methyl-3-(trifluoromethyl)pyrazol-5-yl]oxy}-6-[(m-tolyloxy)methyl]pyridine;

2-{[1-methyl-3-(trifluoromethyl)pyrazol-5-yl]oxy}-6-[(p-tolyloxy)methyl]pyridine;

2-[(3,5-difluorophenoxy)methyl]-6-{[1-methyl-3-(trifluoromethyl)pyrazol-5-yl]oxy}pyridine;

2-{[1-methyl-3-(trifluoromethyl)pyrazol-5-yl]oxy}-6-[(α,α,α-trifluoro-m-tolyloxy) methyl]pyridine;

2-{[(2-chloro-4-pyridyl)oxy]methyl}-6-{[1-methyl-3-(trifluoromethyl)pyrazol-5-yl]oxy}pyridine; and 2-{[1-methyl-3-(trifluoromethyl)pyrazol-5-yl]oxy}-6-{{[1-methyl-3-(trifluoromethyl)pyrazol-5-yl]oxy}methyl}-pyridine, among others.

Exemplary of halogen hereinabove are fluorine, chlorine, bromine and iodine. The terms "$C_1-C_6$haloalkyl", "$C_1-C_4$haloalkyl", "$C_1-C_6$haloalkoxy", "$C_1-C_4$haloalkoxy" and "$C_1-C_4$haloalkylsulfonyl" are defined as a $C_1-C_6$alkyl group, a $C_1-C_4$alkyl group, a $C_1-C_6$alkoxy group, a $C_1-C_4$alkoxy group and a $C_1-C_4$alkylsulfonyl group substituted with one or more halogen atoms, respectively.

The substituted pyridine compounds of the present invention may be prepared by a) reacting a 2-cyano-6-halopyridine of formula II with an alcohol or thiol of formula III and a base such as a metal carbonate or metal hydride in the presence of an inert solvent such as N,N-dimethylformamide, dimethyl sulfoxide, sulfolane, tetrahydrofuran or dioxane, preferably at an elevated temperature, to form a substituted picolinonitrile of formula IV, b) hydrolyzing the substituted picolinonitrile with an acid or base in the presence of water, preferably at an elevated temperature, to form a substituted picolinic acid of formula V, c) reacting the substituted picolinic acid with a phosphorus oxyhalide or thionyl halide at an elevated temperature to form a substituted picolinic acid halide of formula VI, d) reacting the substituted picolinic acid halide with a $C_1-C_4$alcohol and a base such as pyridine or triethylamine in the presence of an inert solvent such as diethyl ether or ethyl acetate to form a substituted picolinate of formula VII, e) reducing the substituted picolinate with a reducing agent such as diisobutyl aluminum hydride or aluminum hydride in the presence of an inert solvent such as diethyl ether and tetrahydrofuran at a temperature range of about −78° C. to 0° C. to form a substituted 2-pyridinemethanol of formula VIII, f) reacting the substituted 2-pyridinemethanol with a phosphorus oxyhalide or thionyl halide to form a substituted 2-halomethylpyridine of formula IX, and g) reacting the substituted 2-halomethylpyridine with an alcohol or thiol of formula X and a base such as a metal carbonate or metal hydride in the presence of an inert solvent such as N,N-dimethylformamide, dimethyl sulfoxide, sulfolane, tetrahydrofuran or dioxane, preferably at an elevated temperature, to form the desired formula I substituted pyridine. The reaction scheme is shown in Flow Diagram I.

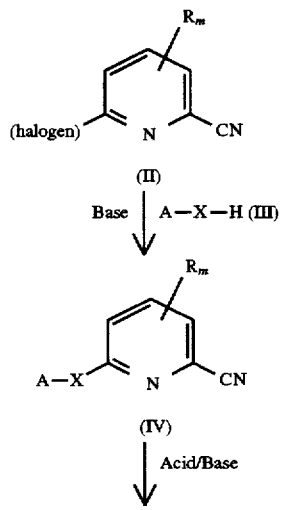

FLOW DIAGRAM I

-continued
FLOW DIAGRAM I

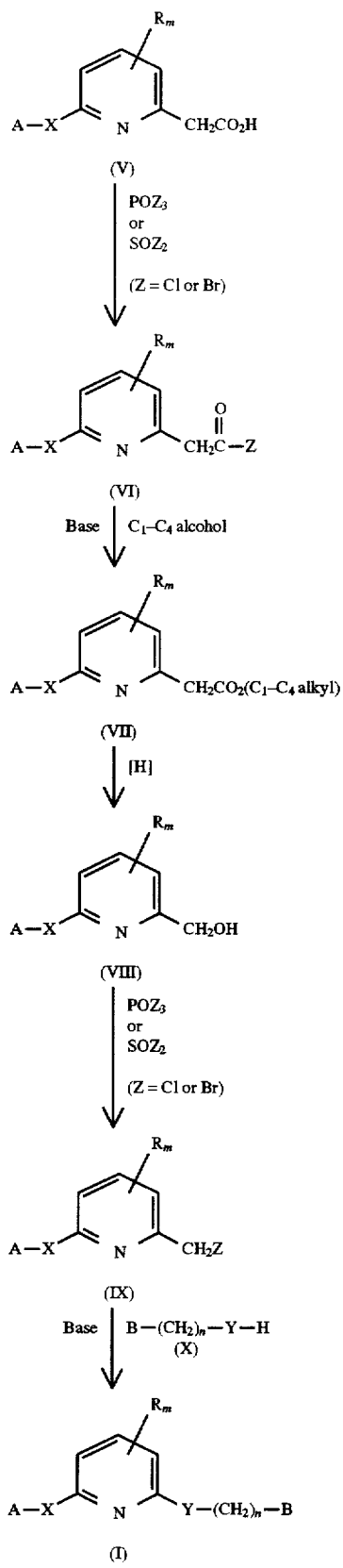

The substituted pyridine compounds of the present invention are effective herbicidal agents useful for the control of a wide variety of undesirable plant species. Those compounds are effective for controlling weeds native to both dry land and wet land areas when applied to the foliage thereof or to soil or water containing seeds or other propagating organs thereof such as stolons, tubers or rhizomes, at rates of from about 0.016 to 4.0 kg/ha and preferably from about 0.1 to 2.0 kg/ha.

While the substituted pyridine compounds of this invention are effective for controlling undesirable plant species when employed alone, they may also be used in combination with other biological chemicals, including other herbicides.

The formula I compounds of this invention may be applied to crops in the form of a solid or liquid herbicidal composition, comprising a herbicidally effective amount of the formula I compound dispersed or dissolved in an agronomically acceptable, inert solid or liquid carrier. The compositions may be applied as preemergence or postemergence treatments.

The formula I compounds may be formulated as emulsifiable concentrates, wettable powders, granular formulations, flowable concentrates and the like.

In order to facilitate a further understanding of the invention, the following examples are presented primarily for the purpose of illustrating more specific details thereof. The invention should not be deemed limited by the examples as the full scope of the invention is defined in the claims.

EXAMPLE 1

Preparation of 6-[(2-Chloro-4-pyridyl)oxy]picolinonitrile

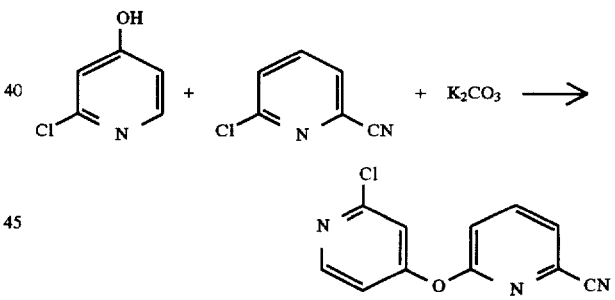

A mixture of 2-chloro-4-hydroxypyridine (38.9 g, 0.3 mol), 2-chloro-6-cyanopyridine (45.7 g, 0.3 mol), and potassium carbonate (45.6 g, 0.3 mol) in N,N-dimethylformamide is refluxed for three hours, cooled and diluted with water and ethyl acetate. The resultant mixture is filtered through a layer of silica gel using ethyl acetate as eluent. The phases are separated and the aqueous phase is extracted with ethyl acetate. The organic extract is combined with the organic phase and the resultant solution is washed with brine, dried over anhydrous magnesium sulfate, and concentrated in vacuo to obtain a residue. Flash column chromatography of the residue using silica gel and a 7:3 hexane/ethyl acetate solution gives the title product as light brown crystals (56.5 g, 81.3%, mp 114° C.).

Using essentially the same procedure, the following compounds are obtained:

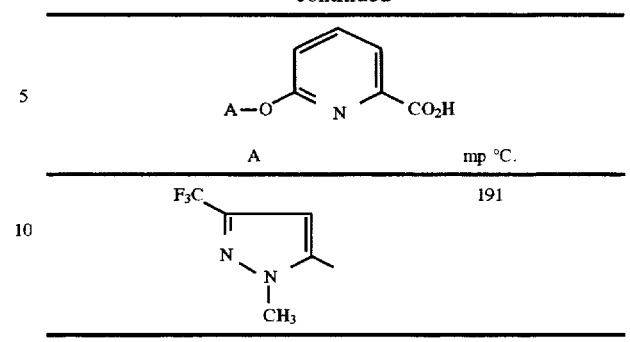

| A | mp °C. |
|---|---|
| 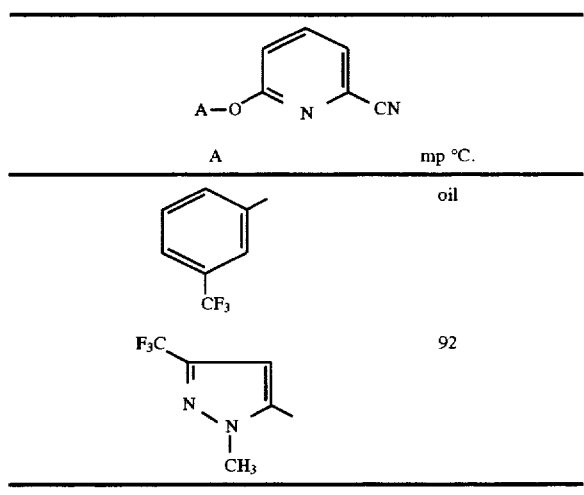 | oil |
| | 92 |

EXAMPLE 2

Preparation of 6-[(2-Chloro-4-pyridyl)oxy]picolinic acid

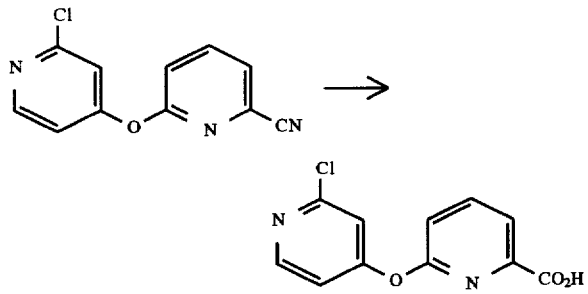

A mixture of 6-[(2-chloro-4-pyridyl)oxy]picolino-nitrile (56.2 g, 0.24 mol) in concentrated hydrochloric acid (60 mL) is refluxed for three hours, cooled and basified to a pH value greater than 10 with 50% sodium hydroxide solution. The resultant solution is washed three times with diethyl ether and acidified with concentrated hydrochloric acid to form a precipitate. The precipitate is collected, washed with water and recrystallized from isopropanol to give the title product as colorless crystals (28 g, 46.6%, mp 183° C.).

Using essentially the same procedure, the following compounds are obtained:

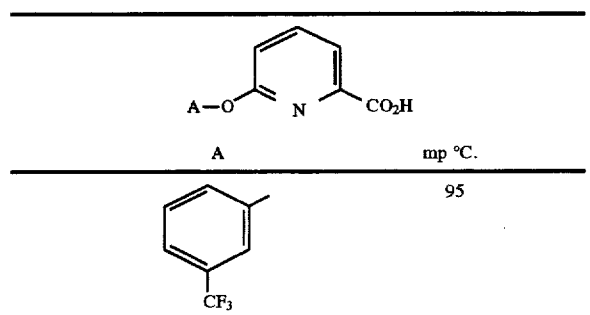

| A | mp °C. |
|---|---|
| | 95 |

| A | mp °C. |
|---|---|
| | 191 |

EXAMPLE 3

Preparation of Methyl 6-[(2-chloro-4-pyridyl)oxy]-picolinate

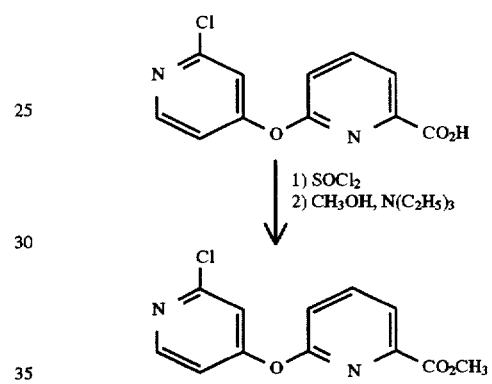

A mixture of 6-[(2-chloro-4-pyridyl)oxy]picolinic acid (28 g, 0.11 mol) and thionyl chloride (50 mL) is refluxed for two hours and concentrated in vacuo to remove residual thionyl chloride. A solution of the resultant acid chloride in ethyl acetate is cooled, treated with triethylamine (55 mL, 0.4 mol) and anhydrous methanol (5.4 mL, 0.13 mol), stirred at room temperature for three hours, and diluted with water. The organic layer is separated, dried over anhydrous magnesium sulfate, and concentrated in vacuo to obtain a residue. Flash column chromatography of the residue using silica gel and a 1:1 hexane/ethyl acetate solution gives the title product as light green crystals (18.1 g, 62.3%, mp 89° C.).

Using essentially the same procedure, the following compounds are obtained:

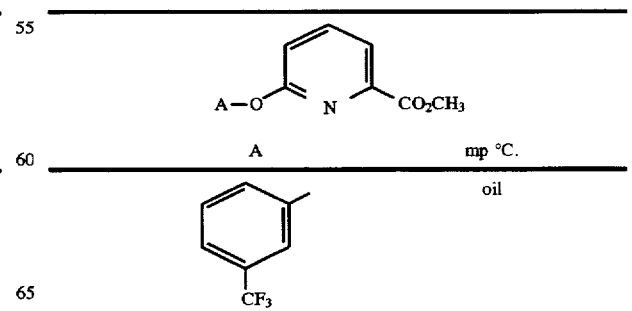

| A | mp °C. |
|---|---|
| | oil |

-continued

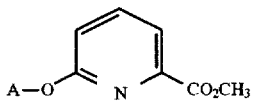

| A | mp °C. |
|---|---|
| 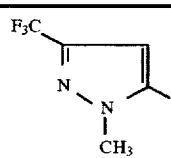 | 108 |

EXAMPLE 4

Preparation of 6-[(2-Chloro-4-pyridyl)oxy]-2-pyridinemethanol

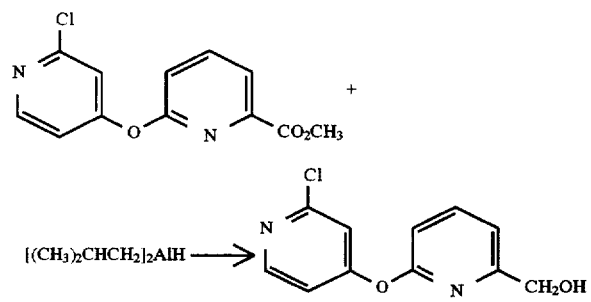

A one molar solution of diisobutylaluminum hydride in tetrahydrofuran (200 mL, 0.2 mol) is added over 45 minutes to a solution of methyl 6-[(2-chloro-4-pyridyl)-oxy] picolinate (18.15 g, 0.069 mol) in diethyl ether (300 mL) at −50° C. Under a nitrogen atmosphere. The reaction mixture is stirred at −50° C. for two hours, allowed to warm to 0° C., and acidified with dilute hydrochloric acid. The phases are separated and the aqueous phase is extracted with diethyl ether. The organic extracts are combined with the organic phase and the resultant solution is washed with saturated sodium hydrogen carbonate solution, dried over anhydrous magnesium sulfate, and concentrated in vacuo to obtain an oil. Flash column chromatography of the oil using silica gel and a 7:3 hexane/ethyl acetate solution gives the title product as a colorless oil (10.2 g, 62.5%).

Using essentially the same procedure, the following compounds are obtained:

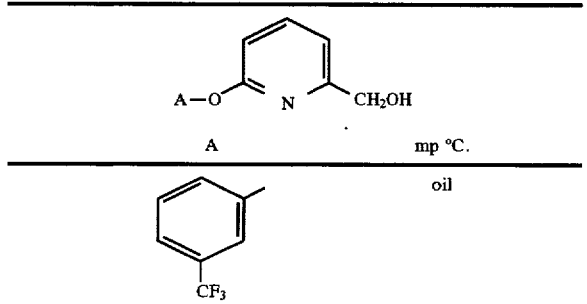

| A | mp °C. |
|---|---|
| 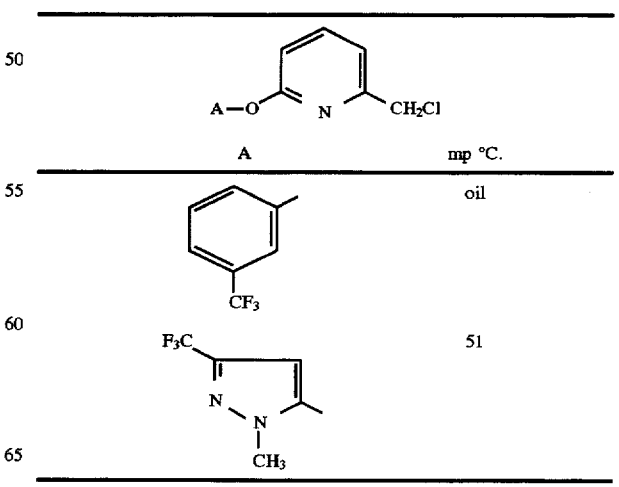 | oil |

-continued

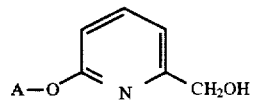

| A | mp °C. |
|---|---|
| 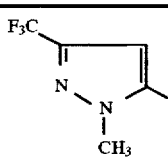 | oil |

EXAMPLE 5

Preparation of 2-(Chloromethyl)-6-[(2-chloro-4-pyridyl)oxy]pyridine

A mixture of 6-[(2-chloro-4-pyridyl)oxy]-2-pyridine-methanol (10.2 g, 0.043 mol) and thionyl chloride (10 mL) is stirred at room temperature for 90 minutes. Excess thionyl chloride is hydrolyzed by adding water to the reaction mixture until no further reaction is observed. The reaction mixture is then neutralized with saturated sodium hydrogen carbonate solution and extracted with dichloromethane. The organic extracts are combined, dried over anhydrous magnesium sulfate, and concentrated in vacuo to obtain the title product (10.6 g, 97%).

Using essentially the same procedure, the following compounds are obtained:

EXAMPLE 6

Preparation of 2-[(2-Chloro-4-pyridyl)oxy]-6-[(p-fluorophenoxy)methyl]pyridine

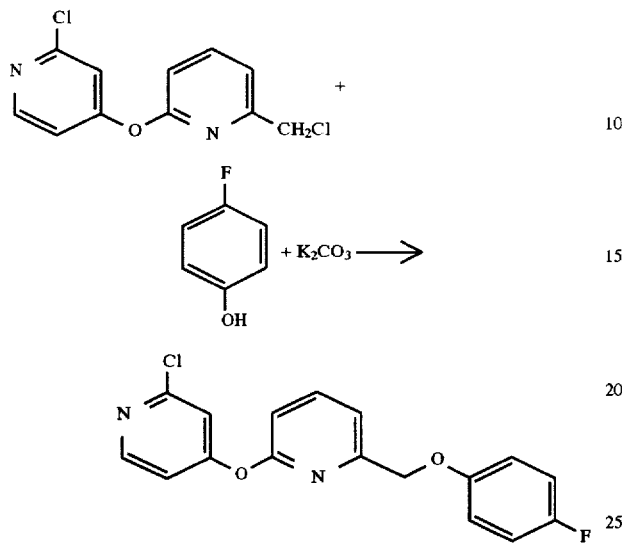

A mixture of 2-(chloromethyl)-6-[(2-chloro-4-pyridyl)oxy]pyridine (1.66 g, 6.5 mmol), 4-fluorophenol (0.89 g, 8 mmol), and potassium carbonate (1.1 g, 8 mmol) in N,N-dimethylformamide (5 mL) is refluxed for 90 minutes, cooled, and diluted with a 1:1 hexane/ethyl acetate solution (100 mL). The organic mixture is then filtered through a layer of silica gel using a 1:1 hexane/ethyl acetate solution as eluent. The resultant solution is concentrated in vacuo to obtain an oil. Flash column chromatography of the oil using silica gel and a 8:2 hexane/ethyl acetate solution gives the title product as colorless crystals (1.5 g, 70%, mp 103° C.).

Using essentially the same procedure, the following compounds are obtained:

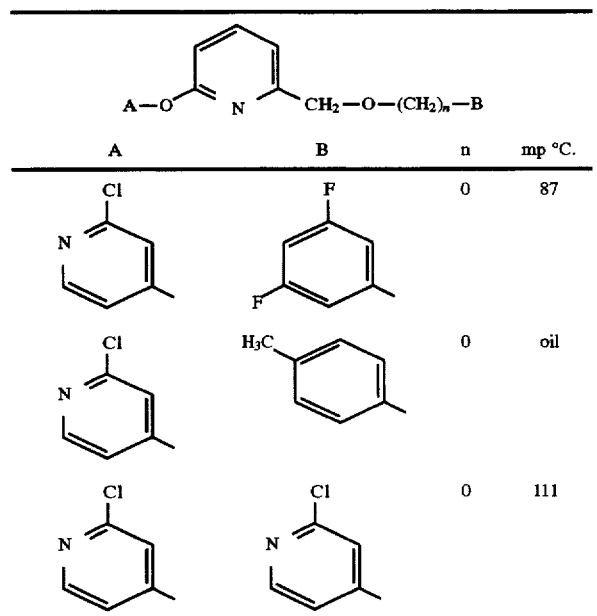

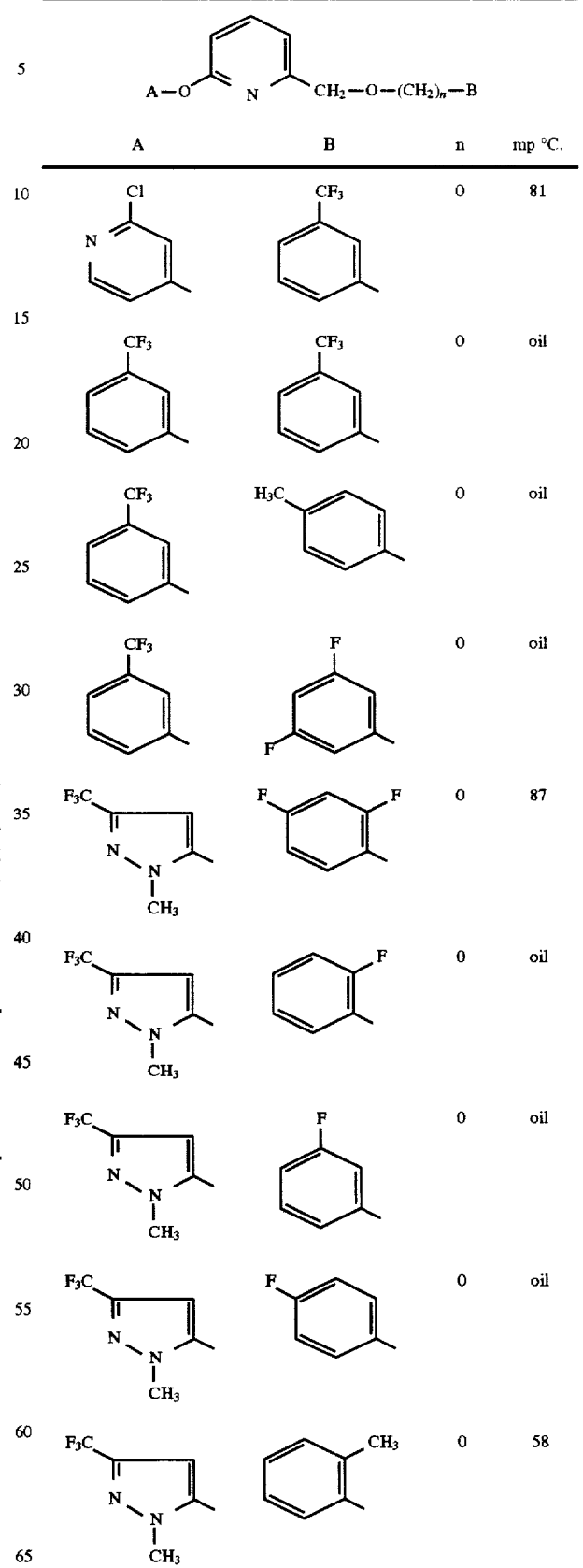

-continued $$A-O-\underset{N}{\underset{|}{\bigcirc}}-CH_2-O-(CH_2)_n-B$$

| A | B | n | mp °C. |
|---|---|---|---|
| 3-CF₃-1-methylpyrazol-5-yl | 3-methylphenyl | 0 | oil |
| 3-CF₃-1-methylpyrazol-5-yl | 4-methylphenyl | 0 | oil |
| 3-CF₃-phenyl | 3-methylphenyl | 0 | oil |
| 3-CF₃-phenyl | 2-chloropyridin-4-yl | 0 | oil |
| 3-CF₃-phenyl | 6-chloropyridin-2-yl | 0 | oil |
| 3-CF₃-phenyl | 3-CF₃-1-methylpyrazol-5-yl | 0 | oil |
| 3-CF₃-phenyl | 2-fluorophenyl | 0 | oil |
| 3-CF₃-phenyl | 2-methylphenyl | 0 | oil |
| 3-CF₃-phenyl | 2,4-difluorophenyl | 0 | oil |
| 3-CF₃-phenyl | 3-fluorophenyl | 0 | oil |

-continued $$A-O-\underset{N}{\underset{|}{\bigcirc}}-CH_2-O-(CH_2)_n-B$$

| A | B | n | mp °C. |
|---|---|---|---|
| 3-CF₃-phenyl | 4-fluorophenyl | 0 | oil |
| 3-CF₃-1-methylpyrazol-5-yl | 3,5-difluorophenyl | 0 | 45 |
| 3-CF₃-1-methylpyrazol-5-yl | 3-CF₃-phenyl | 0 | 76 |
| 3-CF₃-1-methylpyrazol-5-yl | 2-chloropyridin-4-yl | 0 | oil |
| 3-CF₃-1-methylpyrazol-5-yl | 6-chloropyridin-2-yl | 0 | oil |
| 3-CF₃-1-methylpyrazol-5-yl | 3-CF₃-1-methylpyrazol-5-yl | 0 | 93 |
| 3-CF₃-1-methylpyrazol-5-yl | 5-chloropyridin-3-yl | 0 | oil |
| 3-CF₃-1-methylpyrazol-5-yl | 2-chlorophenyl | 0 | 58 |
| 3-CF₃-1-methylpyrazol-5-yl | 3-chlorophenyl | 0 | oil |

-continued

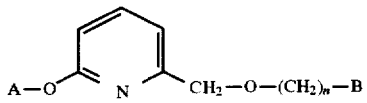

| A | B | n | mp °C. |
|---|---|---|---|
| 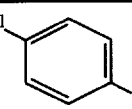 | 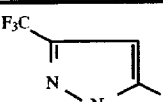 | 0 | oil |
| 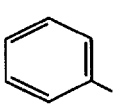 | 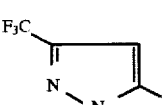 | 1 | oil |

EXAMPLE 7

Postemergence herbicidal evaluation of test compounds

The postemergence herbicidal activity of the compounds of the present invention is demonstrated by the following tests, wherein a variety of dicotyledonous and monocotyledonous seedling plants are sprayed with formulations containing test compounds. The test compounds are dispersed in an acetone solution containing 0.4% by weight of TRITON®X-155, an alkylphenyl ethylene oxide condensate available from Union Carbide Corporation, Danbury, Conn. The acetone mixtures are then diluted with water to provide the equivalent of about 0.48, 0.30 or 0.24 kg per hectare of test compound in a volume equivalent to 400 liters per hectare, and sprayed onto the seedling plants. After spraying, the plants are placed on greenhouse benches and are cared for in the usual manner, commensurate with conventional greenhouse practices. Twenty days after treatment, the seedling plants are examined and rated on a 0–9 scale.

The scale is based upon a visual observation of plant stand, vigor, malformation, size, chlorosis and overall plant appearances as compared with a control. A rating of 0 indicates no herbicidal effect and a rating of 9 indicates complete kill.

Data obtained are reported in Table I below. A dash indicates that the test was not conducted.

Plant species employed in these evaluations are reported by header abbreviation and scientific name.

Compounds employed in this postemergence herbicidal evaluation and in the preemergence evaluation in the following example are given a compound number and identified by name. Data in Table I are reported by compound number.

PLANT SPECIES EMPLOYED IN HERBICIDAL EVALUATIONS

| Header Abbreviation | Scientific Name |
|---|---|
| TRZAS | Triticum aestivum |
| HORVW | Hordeum vulgare |
| GOSHI | Gossipium hirsutum |
| HELAN | Helianthus anuus |
| ZEAMX | Zea mays |
| ALOMY | Alopercurus myosuroides |
| ECHCG | Echinocloa crus-galli |
| SETVI | Setaria viridis |
| GALAP | Galium aparine |
| STEME | Stellaria media |
| VERPE | Veronica persica |
| LAMPU | Lamium purpureum |
| VIOAR | Viola arvensis |
| SIDSP | Sida spinosa |
| AMBAR | Ambrosia artemesifolia |
| ABUTH | Abutilon Theophrasti |
| IPOPU | Ipomea purpurea |
| AMARE | Amaranthus retroflexus |

COMPOUNDS EVALUATED AS HERBICIDAL AGENTS

| Compound Number | |
|---|---|
| 1 | 2-[(2-Chloro-4-pyridyl)oxy]-6-[(p-fluorophenoxy)-methyl]pyridine |
| 2 | 2-[(2-Chloro-4-pyridyl)oxy]-6-[(3,5-difluorophenoxy)-methyl]pyridine |
| 3 | 2-[(2-Chloro-4-pyridyl)oxy]-6-[(p-tolyloxy)methyl]pyridine |
| 4 | 2-[(2-Chloro-4-pyridyl)oxy]-6-{[(2-chloro-4-pyridyl)oxy]-methyl}pyridine |
| 5 | 2-[(2-Chloro-4-pyridyl)oxy]-6-{[(α,α,α-trifluoro-m-tolyl)oxy]methyl}pyridine |
| 6 | 2-[(α,α,α-Trifluoro-m-tolyl)oxy]-6-{[(α,α,α-trifluoro-m-tolyl)oxy]methyl}pyridine |
| 7 | 2-{[(2-Chloro-4-pyridyl)oxy]methyl}-6-[(α,α,α-trifluoro-m-tolyl)oxy]pyridine |
| 8 | 2-{[(6-Chloro-2-pyridyl)oxy]methyl}-6-[(α,α,α-trifluoro-m-tolyl)oxy]pyridine |
| 9 | 2-{{[1-Methyl-3-(trifluoromethyl)pyrazol-5-yl]oxy}-methyl}-6-[(α,α,α-trifluoro-m-tolyl)oxy]pyridine |
| 10 | 2-[(o-Fluorophenoxy)methyl]-6-[(α,α,α-trifluoro-m-tolyl)oxy]pyridine |
| 11 | 2-[(α,α,α-Trifluoro-m-tolyl)oxy]-6-[(o-tolyloxy)methyl]-pyridine |
| 12 | 2-[(2,4-Difluorophenoxy)methyl]-6-[(α,α,α-trifluoro-m-tolyl)oxy]pyridine |
| 13 | 2-[(m-Fluorophenoxy)methyl]-6-[(α,α,α-trifluoro-m-tolyl)-oxy]pyridine |
| 14 | 2-[(p-Fluorophenoxy)methyl]-6-[(α,α,α-trifluoro-m-tolyl)-oxy]pyridine |
| 15 | 2-[(m-Tolyloxy)methyl]-6-[(α,α,α-trifluoro-m-tolyl)oxy]-pyridine |
| 16 | 2-[(p-Tolyloxy)methyl]-6-[(α,α,α-trifluoro-m-tolyl)oxy]-pyridine |
| 17 | 2-[(3,5-Difluorophenoxy)methyl]-6-[(α,α,α-trifluoro-m-tolyl)oxy]pyridine |
| 18 | 2-[(2,4-Difluorophenoxy)methyl]-6-{[1-methyl-3-(trifluoromethyl)pyrazol-5-yl]oxy}pyridine |
| 19 | 2-[(o-Fluorophenoxy)methyl]-6-{[1-methyl-3-(trifluoromethyl)pyrazol-5-yl]oxy}pyridine |
| 20 | 2-[(m-Fluorophenoxy)methyl]-6-{[1-methyl-3-(trifluoromethyl)pyrazol-5-yl]oxy}pyridine |
| 21 | 2-[(p-Fluorophenoxy)methyl]-6-{[1-methyl-3-(trifluoromethyl)pyrazol-5-yl]oxy}pyridine |
| 22 | 2-{[1-Methyl-3-(trifluoromethyl)pyrazol-5-yl]oxy}-6-[(o-tolyloxy)methyl]pyridine |
| 23 | 2-{[1-Methyl-3-(trifluoromethyl)pyrazol-5-yl]oxy}-6-[(m-tolyloxy)methyl]pyridine |
| 24 | 2-{[1-Methyl-3-(trifluoromethyl)pyrazol-5-yl]oxy}-6-[(p-tolyloxy)methyl]pyridine |
| 25 | 2-[(3,5-Difluorophenoxy)methyl]-6-{[1-methyl-3-(trifluoromethyl)pyrazol-5-yl]oxy}pyridine |
| 26 | 2-{[1-Methyl-3-(trifluoromethyl)pyrazol-5-yl]oxy}-6-[(α,α,α-trifluoro-m-tolyloxy)methyl]pyridine |

-continued

| Compound Number | |
|---|---|
| 27 | 2-{[(2-Chloro-4-pyridyl)oxy]methyl}-6-{[1-methyl-3-(trifluoromethyl)pyrazol-5-yl]oxy}pyridine |
| 28 | 2-{[(6-Chloro-2-pyridyl)oxy]methyl}-6-{[1-methyl-3-(trifluoromethyl)pyrazol-5-yl]oxy}pyridine |
| 29 | 2-{[1-Methyl-3-(trifluoromethyl)pyrazol-5-yl]oxy}-6-{{[1-methyl-3-(trifluoromethyl)pyrazol-5-yl]oxy}methyl}-pyridine |
| 30 | 2-{[(5-Chloro-3-pyridyl)oxy]methyl}-6-{[1-methyl-3-(trifluoromethyl)pyrazol-5-yl)oxy}pyridine |
| 31 | 2-[(o-Chlorophenoxy)methyl]-6-{[1-methyl-3-(trifluoromethyl)pyrazol-5-yl]oxy}pyridine |
| 32 | 2-[(m-Chlorophenoxy)methyl]-6-{[1-methyl-3-(trifluoromethyl)pyrazol-5-yl]oxy}pyridine |
| 33 | 2-[(p-Chlorophenoxy)methyl]-6-{[1-methyl-3-(trifluoromethyl)pyrazol-5-yl]oxy}pyridine |
| 34 | 2-[(Benzyloxy)methyl]-6-{[1-methyl-3-(trifluoromethyl)-pyrazol-5-yl]oxy}pyridine |

TABLE I

Postemergence Herbicidal Evaluations of Test Compounds

| Compound Number | Rate (kg/ha) | TRZAS | HORVW | GOSHI | HELAN | ZEAMX | ALOMY | ECHCG | SETVI | GALAP | STEME | VERPE | LAMPU | VIOAR | SIDSP | AMBEL | ABUTH | IPOPU | AMARE |
|---|---|---|---|---|---|---|---|---|---|---|---|---|---|---|---|---|---|---|---|
| 1 | 0.30 | 0 | 0 | 1 | 2 | 0 | 0 | 0 | 0 | 1 | 1 | 1 | — | 2 | 1 | 1 | 1 | 1 | 3 |
| 2 | 0.30 | 0 | 0 | 1 | 2 | 1 | 0 | 0 | 0 | 2 | 1 | 1 | — | 2 | 3 | — | — | 2 | 3 |
| 3 | 0.30 | 1 | 1 | 0 | 1 | 3 | 1 | — | 2 | 1 | 1 | 2 | — | 2 | 1 | 1 | 0 | 1 | 2 |
| 4 | 0.30 | 0 | 0 | 3 | 3 | 3 | 0 | — | 1 | 2 | — | 1 | — | 5 | — | — | — | 2 | — |
| 5 | 0.30 | 0 | 2 | 4 | 4 | 3 | 0 | 3 | 2 | 5 | 4 | 4 | 3 | 7 | 5 | 3 | 4 | 4 | 5 |
| 6 | 0.48 | 3 | 0 | 4 | 4 | 2 | 2 | 3 | 3 | 4 | 4 | 5 | 4 | 7 | 5 | 3 | 4 | 4 | 5 |
| 7 | 0.48 | 3 | 2 | 5 | 4 | 2 | 4 | 1 | 1 | 5 | 4 | 3 | 3 | 5 | 4 | — | 3 | 4 | 4 |
| 8 | 0.48 | 0 | 0 | 3 | 3 | 1 | 3 | — | 2 | 4 | — | 3 | 1 | 4 | — | — | 2 | 2 | — |
| 9 | 0.30 | 0 | 0 | 2 | 3 | 0 | 0 | — | 0 | 0 | — | 0 | 0 | 3 | — | — | 0 | 1 | — |
| 10 | 0.30 | 0 | 0 | 2 | 2 | 0 | 0 | — | 1 | 0 | — | 1 | 0 | 1 | — | — | 0 | 2 | — |
| 11 | 0.30 | 0 | 0 | 2 | 4 | 0 | 0 | — | 0 | 0 | — | 2 | 0 | 2 | — | — | 0 | 2 | — |
| 12 | 0.30 | 0 | 0 | 2 | 3 | 0 | 0 | — | 0 | 0 | — | 1 | 0 | 6 | — | — | 0 | 2 | — |
| 13 | 0.30 | 0 | 0 | 4 | 4 | 0 | 0 | — | 1 | 0 | — | 1 | 0 | 6 | — | — | 0 | 2 | — |
| 14 | 0.30 | 1 | 0 | 2 | 2 | 0 | 1 | — | 0 | 0 | — | 2 | 1 | 4 | — | — | 0 | 2 | — |
| 15 | 0.30 | 0 | 0 | 4 | 3 | 0 | 0 | — | 1 | 0 | — | 1 | 0 | — | — | — | 0 | 2 | — |
| 16 | 0.30 | 0 | 0 | 4 | 2 | 0 | 0 | — | 0 | 0 | — | 2 | 0 | 6 | — | — | 0 | 2 | — |
| 17 | 0.30 | 0 | 0 | 2 | 1 | 0 | 0 | — | 0 | 0 | — | 0 | — | 6 | — | — | 0 | 2 | — |
| 18 | 0.30 | 0 | 0 | 5 | 3 | 0 | 1 | — | 1 | 0 | — | 6 | 0 | — | 0 | 4 | 5 | 3 | 5 |
| 19 | 0.30 | 2 | 4 | 2 | 2 | 3 | 2 | 0 | 5 | 4 | 4 | 8 | 4 | — | — | 0 | 0 | 4 | 5 |
| 20 | 0.30 | 3 | 4 | 2 | 4 | 3 | 3 | — | 3 | 5 | 4 | 5 | 3 | 5 | 4 | 3 | 3 | 4 | 4 |
| 21 | 0.48 | 2 | 2 | 1 | 5 | 3 | 4 | — | 3 | 3 | 1 | 7 | — | 7 | 3 | 3 | 2 | 5 | 4 |
| 22 | 0.30 | 1 | 1 | 2 | 4 | 2 | 1 | — | 2 | 2 | — | 7 | — | 6 | — | — | 0 | 3 | — |
| 23 | 0.30 | 0 | 0 | — | 4 | 0 | 1 | — | 1 | 0 | — | 6 | — | 4 | — | — | 0 | 4 | 2 |
| 24 | 0.30 | 0 | 1 | 2 | 4 | 0 | 1 | — | 1 | 0 | 3 | 7 | — | 4 | 4 | — | 3 | 3 | 2 |
| 25 | 0.30 | 0 | 1 | 4 | 4 | 0 | 1 | 1 | 1 | 4 | 1 | 6 | — | 2 | 3 | 3 | 2 | 2 | 2 |
| 26 | 0.30 | 0 | 0 | 4 | 3 | 1 | 1 | 1 | 1 | 3 | 0 | 4 | — | 3 | 1 | 1 | 0 | 3 | 3 |
| 27 | 0.30 | 0 | 1 | 3 | 4 | 1 | 2 | 0 | 1 | 3 | 1 | 3 | — | 1 | 1 | 1 | 0 | 2 | — |
| 28 | 0.30 | 1 | 1 | 3 | 4 | 0 | 1 | 0 | 1 | 3 | 0 | 4 | — | 1 | — | 2 | 3 | 3 | — |
| 29 | 0.30 | 0 | 0 | 4 | 3 | 1 | 1 | — | 1 | 1 | 1 | 1 | — | 1 | — | — | 1 | 0 | — |
| 30 | 0.30 | 0 | 1 | 3 | 3 | 0 | 1 | — | 1 | 1 | 0 | 1 | — | 1 | — | — | 1 | 3 | — |
| 31 | 0.30 | 0 | 0 | 2 | 3 | 3 | 0 | — | 0 | 2 | 0 | 2 | — | 5 | — | — | — | 3 | — |
| 32 | 0.30 | 0 | 0 | 2 | 3 | 3 | 0 | — | 1 | 2 | — | 2 | — | 7 | — | — | — | 0 | — |
| 33 | 0.30 | 0 | 0 | 2 | 3 | 3 | 0 | — | 2 | 2 | — | 3 | — | 7 | — | — | — | 3 | — |
| 34 | 0.24 | 2 | 1 | 3 | 2 | 2 | 1 | — | 0 | 3 | — | 3 | — | 6 | — | — | 0 | — | — |

EXAMPLE 8

Preemergence herbicidal evaluation of test compounds

The preemergence herbicidal activity of the test compounds of the present invention is exemplified by the following tests in which the seeds of a variety of monocotyledonous and dicotyledonous plants are separately mixed with potting soil and planted on top of soil in separate containers. After planting, the cups are sprayed with the formulations described in Example 7 to provide the equivalent of about 0.48 kg or 0.30 kg per hectare of test compound per container. The treated containers are then placed on greenhouse benches and cared for in accordance with conventional greenhouse procedures. Twenty days after treatment, the tests are terminated and each container is examined and rated according to the rating system provided in Example 7.

Data obtained are reported in Table II below. A dash indicates that the test was not conducted. The compounds evaluated are reported by compound number given in Example 7.

TABLE II

Preemergence Herbicidal Evaluations of Test Compounds

| Compound Number | Rate (kg/ha) | TRZAS | HORVW | GOSHI | HELAN | ZEAMX | ALOMY | ECHCG | SETVI | GALAP | STEME | VERPE | LAMPU | VIOAR | SIDSP | AMBEL | ABUTH | IPOPU | AMARE |
|---|---|---|---|---|---|---|---|---|---|---|---|---|---|---|---|---|---|---|---|
| 1 | 0.30 | 0 | 0 | 0 | 0 | 0 | 0 | 0 | 1 | 0 | 0 | 5 | 0 | 2 | 0 | 0 | 0 | 0 | 4 |
| 2 | 0.30 | 0 | 0 | 0 | 0 | 0 | 0 | 0 | 0 | 0 | 0 | 2 | 0 | 1 | 0 | 0 | 0 | 0 | 1 |
| 3 | 0.30 | 0 | 0 | 0 | 0 | 0 | 0 | 0 | 0 | 0 | 0 | 1 | 0 | 0 | 0 | 0 | 0 | 0 | 0 |
| 4 | 0.30 | 0 | 0 | 0 | 0 | 0 | 0 | — | — | 0 | 0 | 9 | — | 3 | — | — | — | 1 | — |
| 5 | 0.48 | 0 | 0 | 0 | — | 0 | 0 | — | 6 | 0 | 0 | 1 | 0 | 5 | — | 0 | 0 | 0 | 7 |
| 6 | 0.48 | 0 | 0 | 2 | 0 | 0 | 0 | 1 | 2 | 0 | 0 | 0 | 2 | 0 | — | 1 | 0 | 0 | 7 |
| 7 | 0.48 | 0 | 0 | 0 | — | 0 | 0 | 2 | 4 | 0 | 0 | 1 | 0 | 0 | — | 0 | 0 | 1 | 1 |
| 8 | 0.48 | 0 | 0 | 0 | 0 | 0 | 0 | 0 | 0 | 0 | — | 0 | 0 | — | — | — | — | 0 | — |
| 9 | 0.30 | 0 | 0 | 0 | 0 | 0 | 0 | — | 0 | 0 | — | 1 | 0 | 0 | — | — | — | 0 | — |
| 10 | 0.30 | 0 | 0 | 0 | 0 | 0 | 0 | — | 0 | 0 | — | 0 | 0 | 0 | — | — | — | 0 | — |
| 11 | 0.30 | 0 | 0 | 0 | 0 | 0 | 0 | — | 0 | 0 | — | 1 | 0 | 0 | — | — | — | 0 | — |
| 12 | 0.30 | 0 | 0 | 0 | 0 | 0 | 0 | — | 0 | 0 | — | 1 | 0 | 0 | — | — | — | 0 | — |
| 13 | 0.30 | 0 | 0 | 0 | 0 | 0 | 0 | — | 0 | 0 | — | 0 | 0 | 2 | — | — | — | 0 | — |
| 14 | 0.30 | 0 | 0 | 0 | 0 | 0 | 0 | — | 0 | 0 | — | 1 | 0 | 1 | — | — | — | 0 | — |
| 15 | 0.30 | 0 | 0 | 0 | 0 | 0 | 0 | — | 0 | 0 | — | 1 | 0 | 0 | — | — | — | 0 | — |
| 16 | 0.30 | 0 | 0 | 0 | 0 | 0 | 0 | — | 0 | 0 | — | 0 | 0 | 0 | 0 | 0 | 0 | 0 | — |
| 17 | 0.30 | 0 | 0 | 0 | 0 | 0 | 0 | — | 0 | 0 | — | 1 | 0 | 6 | — | — | — | 2 | 8 |
| 18 | 0.30 | 1 | 2 | — | 2 | 0 | 1 | 0 | 3 | 3 | 6 | 7 | 0 | 7 | 0 | 1 | 3 | 1 | 9 |
| 19 | 0.30 | 0 | 0 | 1 | 0 | 0 | 2 | 3 | 0 | 2 | 4 | 5 | — | 5 | — | — | 0 | 0 | 8 |
| 20 | 0.30 | 1 | 2 | — | 0 | 1 | 4 | 0 | 0 | 1 | 0 | 9 | 0 | — | 0 | 0 | 0 | 0 | 7 |
| 21 | 0.48 | 0 | 0 | — | 0 | 0 | 0 | 4 | 3 | 3 | — | 9 | — | 8 | — | — | 0 | 2 | — |
| 22 | 0.30 | 0 | 0 | 0 | 0 | 0 | 0 | 0 | 0 | 0 | — | 8 | 0 | — | — | — | 0 | 1 | — |
| 23 | 0.30 | 0 | 0 | 0 | 0 | 0 | 0 | 3 | 0 | 0 | 3 | 7 | 4 | 1 | 0 | 0 | 0 | 0 | 6 |
| 24 | 0.30 | 2 | 2 | 0 | 2 | 0 | 1 | 0 | 7 | 0 | 4 | 6 | 4 | 7 | 0 | 0 | 0 | 0 | 0 |
| 25 | 0.30 | 0 | 0 | 0 | 0 | 0 | 0 | 4 | 2 | 0 | 0 | 8 | 4 | 5 | 0 | — | 0 | 0 | 6 |
| 26 | 0.30 | 2 | 0 | 0 | 0 | 0 | 1 | — | 2 | 0 | 3 | 9 | 0 | 8 | 0 | 1 | 0 | 1 | 0 |
| 27 | 0.30 | 0 | 0 | 0 | 2 | 0 | 0 | — | 1 | 0 | 4 | 9 | 5 | 4 | 0 | 1 | 0 | 0 | 6 |
| 28 | 0.30 | 0 | 0 | 0 | 0 | 0 | 1 | — | 1 | 0 | 0 | 7 | 0 | 7 | 0 | — | 0 | 2 | 0 |
| 29 | 0.30 | 0 | 0 | 0 | 0 | 0 | 0 | — | 1 | 0 | 0 | 9 | 0 | 0 | 0 | 0 | 0 | 0 | 0 |
| 30 | 0.30 | 0 | 0 | 0 | 0 | 0 | 2 | — | 1 | 0 | 0 | 0 | 0 | 0 | 0 | 0 | 0 | 0 | — |
| 31 | 0.30 | 0 | 0 | 0 | 0 | 0 | 0 | — | 1 | 0 | 0 | 5 | 5 | 3 | — | — | — | 0 | — |
| 32 | 0.30 | 0 | 0 | 0 | 0 | 0 | 0 | — | 1 | 0 | 0 | 3 | — | 3 | — | — | — | 0 | — |
| 33 | 0.30 | 0 | 0 | 0 | 0 | 0 | 0 | — | 1 | 0 | 0 | 5 | 0 | 2 | — | — | — | 0 | — |
| 34 | 0.48 | 1 | 4 | 0 | 0 | 3 | 4 | — | 7 | 0 | — | 5 | — | — | — | 0 | — | — | — |

What is claimed is:
1. A compound having the structural formula

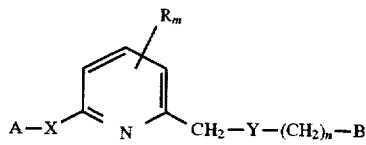

wherein
one of the groups A and B represents
  phenyl optionally substituted with one or more halogen atoms, nitro groups, cyano groups, amino groups, hydroxyl groups, $C_1-C_4$alkyl groups, $C_1-C_4$haloalkyl groups, $C_1-C_4$alkoxy groups, $C_1-C_4$haloalkoxy groups or $C_1-C_4$haloalkylsulfonyl groups, or
  1- or 2-naphthyl optionally substituted with one or more halogen atoms, nitro groups, cyano groups, amino groups, hydroxyl groups, $C_1-C_4$alkyl groups, $C_1-C_4$haloalkyl groups, $C_1-C_4$alkoxy groups, $C_1-C_4$haloalkoxy groups or $C_1-C_4$halo-alkylsulfonyl groups;
the other one of groups A and B represents a pyrazolyl group optionally substituted with one or more halogen atoms, nitro groups, cyano groups, amino groups, hydroxyl groups, $C_1-C_4$alkyl groups, $C_1-C_4$haloalkyl groups, $C_1-C_4$alkoxy groups, $C_1-C_4$haloalkoxy groups or $C_1-C_4$haloalkylsulfonyl groups;
X and Y are each independently O or S;
R is $C_1-C_6$alkyl, $C_1-C_6$haloalkyl, $C_1-C_6$alkoxy, $C_1-C_6$haloalkoxy, $C_1-C_6$alkylthio or di($C_1-C_6$alkyl)amino;
m is an integer of 0, 1 or 2; and
n is an integer of 0 or 1.

2. The compound according to claim 1 wherein
B represents
  phenyl optionally substituted with one or more halogen atoms, $C_1-C_4$alkyl groups, $C_1-C_4$haloalkyl groups, $C_1-C_4$alkoxy groups, $C_1-C_4$haloalkoxy groups or $C_1-C_4$haloalkylsulfonyl groups;
A represents
  a pyrazolyl group optionally substituted with one or more halogen atoms, $C_1-C_4$alkyl groups, $C_1-C_4$haloalkyl groups, $C_1-C_4$alkoxy groups, $C_1-C_4$haloalkoxy groups or $C_1-C_4$haloalkylsulfonyl groups;
R is $C_1-C_4$alkyl, $C_1-C_4$haloalkyl, $C_1-C_4$alkoxy, $C_1-C_4$haloalkoxy, $C_1-C_4$alkylthio or di($C_1-C_4$alkyl)amino; and
m and n are each independently an integer of 0 or 1.

3. The compound according to claim 2 wherein
B represents
  phenyl optionally substituted with one to three halogen atoms, $C_1-C_4$alkyl groups or $C_1-C_4$haloalkyl groups;
A represents
  a pyrazolyl group optionally substituted with one to three halogen atoms, $C_1-C_4$alkyl groups or $C_1-C_4$haloalkyl groups;
X and Y are O; and
R is $C_1-C_4$alkyl, $C_1-C_4$haloalkyl, $C_1-C_4$alkoxy or $C_1-C_4$haloalkoxy.

4. The compound according to claim 3 wherein
A is
  5-pyrazolyl optionally substituted with one or two methyl groups or trifluoromethyl groups;
B is phenyl optionally substituted with one or two fluorine atoms, chlorine atoms, methyl groups or trifluoromethyl groups; and
m and n are 0.

5. A method for controlling undesirable plant species which comprises applying to the foliage of said plants or to the soil or water containing seeds or other propagating organs thereof, a herbicidally effective amount of a compound having the structural formula according to claim 1.

6. The method according to claim 5 wherein
one of groups A and B represents
  phenyl optionally substituted with one or more halogen atoms, $C_1-C_4$alkyl groups, $C_1-C_4$haloalkyl groups, $C_1-C_4$alkoxy groups, $C_1-C_4$haloalkoxy groups or $C_1-C_4$haloalkylsulfonyl groups;
and the other of groups A and B represents
  a pyrazolyl group optionally substituted with one or more halogen atoms, $C_1-C_4$alkyl groups, $C_1-C_4$haloalkyl groups, $C_1-C_4$alkoxy groups, $C_1-C_4$haloalkoxy groups or $C_1-C_4$haloalkylsulfonyl groups;
R is $C_1-C_4$alkyl, $C_1-C_4$haloalkyl, $C_1-C_4$alkoxy, $C_1-C_4$haloalkoxy, $C_1-C_4$alkylthio or di($C_1-C_4$alkyl)amino; and
m and n are each independently an integer of 0 or 1.

7. The method according to claim 6 wherein
B represents
  phenyl optionally substituted with one to three halogen atoms, $C_1-C_4$alkyl groups or $C_1-C_4$haloalkyl groups;
A represents
  a pyrazolyl group optionally substituted with one to three halogen atoms, $C_1-C_4$alkyl groups or $C_1-C_4$haloalkyl groups;
X and Y are O; and
R is $C_1-C_4$alkyl, $C_1-C_4$haloalkyl, $C_1-C_4$alkoxy or $C_1-C_4$haloalkoxy.

8. The method according to claim 7 wherein
A is
  5-pyrazolyl optionally substituted with one or two methyl groups or trifluoromethyl groups;
B is phenyl optionally substituted with one or two fluorine atoms, chlorine atoms, methyl groups or trifluoromethyl groups; and
m and n are 0.

9. The method according to claim 5 which comprises applying said compound to the foliage of said plants or to the soil or water containing seeds or other propagating organs thereof at a rate of about 0.016 kg/ha to 4.0 kg/ha.

10. A herbicidal composition which comprises an inert solid or liquid carrier and a herbicidally effective amount of a compound having the structural formula according to claim 1.

11. The composition according to claim 10 wherein one of groups A and B represents phenyl optionally substituted with one or more halogen atoms, $C_1-C_4$alkyl groups, $C_1-C_4$haloalkyl groups, $C_1-C_4$alkoxy groups, $C_1-C_4$haloalkoxy groups or $C_1-C_4$haloalkylsulfonyl groups;
the other of groups A and B represents
  a pyrazolyl group optionally substituted with one or more halogen atoms, $C_1-C_4$alkyl groups, $C_1-C_4$haloalkyl groups, $C_1-C_4$alkoxy groups, $C_1-C_4$haloalkoxy groups or $C_1-C_4$haloalkylsulfonyl groups;
R is $C_1-C_4$alkyl, $C_1-C_4$haloalkyl, $C_1-C_4$alkoxy, $C_1-C_4$haloalkoxy, $C_1-C_4$alkylthio or di($C_1-C_4$alkyl)amino; and
m and n are each independently an integer of 0 or 1.

12. The composition according to claim 11 wherein
B is
  phenyl optionally substituted with one to three halogen atoms, $C_1-C_4$alkyl groups or $C_1-C_4$haloalkyl groups;

A is a pyrazolyl group optionally substituted with one to three halogen atoms, $C_1$–$C_4$alkyl groups or $C_1$–$C_4$haloalkyl groups;

X and Y are O; and

R is $C_1$–$C_4$alkyl, $C_1$–$C_4$haloalkyl, $C_1$–$C_4$alkoxy or $C_1$–$C_4$haloalkoxy.

13. The composition according to claim 10 wherein A is 5-pyrazolyl optionally substituted with one or two methyl groups or trifluoromethyl groups;

B is phenyl optionally substituted with one or two fluorine atoms, chlorine atoms, methyl groups or trifluoromethyl groups; and m and n are 0.

14. The compound according to claim 4 selected from the group consisting of

2-[(m-fluorophenoxy)methyl]-6-{[1-methyl-3-(trifluoromethyl)pyrazol-5-yl]oxy}-pyridine;

2-[(p-fluorophenoxy)methyl]-6-{[1-methyl-3-(trifluoromethyl)pyrazol-5-yl]oxy}-pyridine:

2-{[1-methyl-3-(trifluoromethyl)pyrazol-5-yl]oxy}-6-[(o-tolyloxy)methyl]pyridine;

2-{[1-methyl-3-(trifluoromethyl)pyrazol-5-yl]oxy}-6-[(m-tolyloxy)methyl]pyridine;

2-{[1-methyl-3-(trifluoromethyl)pyrazol-5-yl]oxy}-6-[(p-tolyloxy)methyl]pyridine;

2-[(3,5-difluorophenoxy)methyl]-6-{[1-methyl-3-(trifluoromethyl)pyrazol-5-yl]oxy}pyridine;

2-{[1-methyl-3-(trifluoromethyl)pyrazol-5-yl]oxy}-6-[(α,α,α-trifluoro-m-tolyloxy)methyl]pyridine;

2-[(o-chlorophenoxy)methyl]-6-{[1-methyl-3-(trifluoromethyl)pyrazol-5-yl]oxy}-pyridine;

2-[(m-chlorophenoxy)methyl]-6-{[1-methyl-3-(trifluoromethyl)pyrazol-5-yl]oxy}-pyridine;

2-[(p-chlorophenoxy)methyl]-6-{[1-methyl-3-(trifluoromethyl)pyrazol-5-yl]oxy}-pyridine; and 2-[(benzyloxy)methyl]-6{[1-methyl-3-(trifluoromethyl)pyrazol-5-yl]oxy}pyridine.

15. The method according to claim 6 wherein the compound is selected from the group consisting of 2-[(m-fluorophenoxy)methyl]-6-{[1-methyl-3-(trifluoromethyl)pyrazol-5-yl]oxy}-pyridine;

2-[(p-fluorophenoxy)methyl]-6-{[1-methyl-3-(trifluoromethyl)pyrazol-5-yl]oxy}-pyridine;

2-{[1-methyl-3-(trifluoromethyl)pyrazol-5-yl]oxy}6-[(o-tolyloxy)methyl]pyridine;

2-{[1-methyl-3-(trifluoromethyl)pyrazol-5-yl]oxy}6-[(m-tolyloxy)methyl]pyridine;

2-{[1-methyl-3-(trifluoromethyl)pyrazol-5-yl]oxy}6-[(p-tolyloxy)methyl]pyridine;

2-[(3,5-difluorophenoxy)methyl]-6-{[1-methyl-3-(trifluoromethyl)pyrazol-5-yl]oxy}pyridine;

2-{[1-methyl-3-(trifluoromethyl)pyrazol-5-yl]oxy}-6-[(α,α,α-trifluoro-m-tolyloxy)methyl]pyridine;

2-[(o-chlorophenoxy)methyl]-6-{[1-methyl-3-(trifluoromethyl)pyrazol-5-yl]oxy}-pyridine;

2-[(m-chlorophenoxy)methyl]-6-{[1-methyl-3-(trifluoromethyl)pyrazol-5-yl]oxy}-pyridine;

2-[(p-chlorophenoxy)methyl]-6-{[1-methyl-3-(trifluoromethyl)pyrazol-5-yl]oxy}-pyridine; and 2-[(benzyloxy)methyl]-6{[1-methyl-3-(trifluoromethyl)pyrazol-5-yl]oxy}pyridine.

16. The compound according to claim 1 wherein

A represents a phenyl group optionally substituted with one or two fluorine atoms, chlorine atoms, methyl groups or trifluoromethyl groups;

B represents a 5-pyrazolyl group optionally substituted with one or two methyl groups or trifluoromethyl groups; and m and n are 0.

17. The compound according to claim 16 which is 2-{{[1-methyl-3-(trifluoromethyl)pyrazol-5-yl]oxy}methyl}-6-(α,α,α-trifluoro-m-tolyloxy)pyridine.

\* \* \* \* \*